United States Patent
Sotos

(10) Patent No.: US 7,395,222 B1
(45) Date of Patent: Jul. 1, 2008

(54) METHOD AND SYSTEM FOR IDENTIFYING EXPERTISE

(76) Inventor: John G. Sotos, 1788 Oak Creek Dr., Apt. 415, Palo Alto, CA (US) 94304

( * ) Notice: Subject to any disclaimer, the term of this patent is extended or adjusted under 35 U.S.C. 154(b) by 1129 days.

(21) Appl. No.: 10/007,156

(22) Filed: Dec. 5, 2001

Related U.S. Application Data

(63) Continuation of application No. 09/948,923, filed on Sep. 7, 2001, now abandoned.

(60) Provisional application No. 60/230,689, filed on Sep. 7, 2000.

(51) Int. Cl.
G06F 17/60 (2006.01)
(52) U.S. Cl. .................................. 705/10; 707/5
(58) Field of Classification Search .................. 705/10
See application file for complete search history.

(56) References Cited

U.S. PATENT DOCUMENTS

| | | | | |
|---|---|---|---|---|
| 5,794,178 | A * | 8/1998 | Caid et al. | 704/9 |
| 5,826,260 | A * | 10/1998 | Byrd et al. | 707/5 |
| 5,862,223 | A * | 1/1999 | Walker et al. | 705/50 |
| 5,911,140 | A * | 6/1999 | Tukey et al. | 707/5 |
| 5,915,249 | A * | 6/1999 | Spencer | 707/5 |
| 5,920,854 | A * | 7/1999 | Kirsch et al. | 707/3 |
| 6,119,114 | A * | 9/2000 | Smadja | 707/7 |
| 6,154,737 | A * | 11/2000 | Inaba et al. | 707/3 |
| 6,223,165 | B1 * | 4/2001 | Lauffer | 705/8 |
| 6,424,963 | B1 * | 7/2002 | Ito et al. | 707/1 |
| 6,738,780 | B2 * | 5/2004 | Lawrence et al. | 707/101 |
| 6,757,676 | B1 * | 6/2004 | Sugaya et al. | 707/5 |
| 6,961,731 | B2 * | 11/2005 | Holbrook | 707/102 |
| 7,010,515 | B2 * | 3/2006 | Nakano | 707/1 |
| 7,167,855 | B1 * | 1/2007 | Koenig | 707/3 |
| 2003/0014428 | A1 * | 1/2003 | Mascarenhas | 707/200 |
| 2005/0278321 | A1 * | 12/2005 | Vailaya et al. | 707/3 |
| 2006/0059138 | A1 * | 3/2006 | Milic-Frayling et al. | 707/3 |
| 2006/0161353 | A1 * | 7/2006 | Mascarenhas | 702/19 |

OTHER PUBLICATIONS

"Healthcentral.com extends content agreement with Yahoo!", PR Newswire, Aug. 31, 2000.*
"Virtual medicine can't replace real thing Many web sites can be valuable sources of consumer health information, but most experts advise against taking online test-for both medical and privacy reasons" by Benedict Carey. Star Tribune, Aug. 27, 2000.*
"Using your PC to pick the best fund finder" by Michael Gianturco, Forbes, v158, n8, Oct. 7, 1996.*

(Continued)

*Primary Examiner*—Beth Van Doren
*Assistant Examiner*—Dave Robertson
(74) *Attorney, Agent, or Firm*—Townsend and Townsend and Crew LLP

(57) ABSTRACT

A system and method of identifying entities having expertise in one or more subjects. Among other features, the method includes querying a database for documents (e.g., articles, papers, periodicals) relevant to a subject; and calculating a first score for each relevant document. The method also identifies entities affiliated with one or more relevant documents; and calculates a second score for each entity based on the one or more first scores of the one or more relevant documents affiliated with the entity. A step of ranking expertise of the entities based on the respective second scores of the entities is included.

24 Claims, 20 Drawing Sheets

OTHER PUBLICATIONS

"IAC launches Insite Pro" Web-based, flat-fee business intelligence solution for information professionals, Business Wire, May 13, 1997.*

Webarchive of www.healthcentral.com from 1999 (8 pages).*

Webarchive of www.nlm.nih.gov from 2000 (8 pages).*

"Healthcentral.com ranked #1 health content website according to Gomez", PR Newswire, Aug. 16, 2000.*

"Healthcentral.com partners with bestdoctors to create exclusive access to medical experts", Business Wire, May 10, 1999.*

"Creating a CD-ROM: overview of the product field (Buyers Guide)" by Bernard Banet, Seybold Report on Desktop Publishing, v7, n6, Feb. 1, 1993.*

Becerra-Fernandez, I. Searchable Answer Generating Environment (SAGE): A Knowledge Management System for Searching for Experts in Florida. Proceedings of the 12 th Annual International Florida Artificial Intelligence Research Symposium (FLAIRS)—Knowledge Management Track, Orlando, Florida (May 1999), (abstract only).*

Becerra-Fernandez, I. The role of artificial intelligence technologies in the implementation of People-Finder knowledge management systems. In Staab, S. & O'Leary, D. (Eds.), Bringing Knowledge to Business Processes. Workshop in the AAAI Spring Symposium Series. Stanford, Mar. 20-22, 2000, Menlo Park, CA. AAAI.*

Becerra-Fernandez, I. "Facilitating the Online Search of Experts at NASA using Expert Seeker People-Finder" in PAKM 2000 Third International Conference on Practical Aspects of Knowledge Management, Proceedings of the Third International Conference Basel, Switzerland, Oct. 30-31, 2000, 7 pgs.*

Becerra-Fernandez, I. Searching for Experts with Expertise-Locator Knowledge Management Systems. In ACL '01 Workshop on Human Language Technology and Knowledge Management, Toulouse, France, 2001.*

Mattox, D., Maybury, M. and Morey, D. 1999. Enterprise Expert and Knowledge Discovery. International Conference on Human Computer International (HCI 99). Aug. 23-27, 1999. Munich, Germany, 303-307.*

Streeter, L. & Lochbaum, K. 1988. An Expert/Expert-Locating System Based on Automatic Representation of Semantic Structure, Proceedings of the Fourth Conference on Artificial Intelligence Applications, San Diego, CA, Mar. 1988, 345-350.*

Consumers' Checkbook. www.checkbook.org, Aug. 2000 (9 pages) [downloaded from www.archive.org on Oct. 15, 2007].*

Becerra-Fernandez, I. Searchable Answer Generating Environment (SAGE): A Knowledge Management System for Searching for Experts in Florida. Proceedings of the 12 th Annual International Florida Artificial Intelligence Research Symposium (FLAIRS)—Knowledge Management Track, Orlando, Florida (May 1999), (full text).*

McDonald, D. W. and Ackerman, M. S. 1998. Just talk to me: a field study of expertise location. In Proceedings of the 1998 ACM Conference on Computer Supported Cooperative Work (Seattle, Washington, United States, Nov. 14-18, 1998).*

Web page, "Acu Match Index," at URL=http://www.bestdoctors.com/en/docfinder/am index.asp, 1 page, printed Apr. 25, 2002.

Web page, "Find a Doctor," at URL=http://www.bestdoctor.com/acumatch/am_processing.asp, 1 page, printed Apr. 25, 2002.

Web page, "Find Best Doctors," at URL=http://www.bestdoctor.com/en/docfinder/fullsearch/find.asp, 1 page, printed Apr. 25, 2002.

Web page, "Frequently Asked Questions," at URL=http://www.bestdoctor.com/en/faq.htm, 1 page, printed Apr. 25, 2002.

Web page, "Methodology," at URL=http://www.bestdoctor.com/en/about/method.htm, 2 pages, printed Apr. 25, 2002.

Web page, "Why We Charge," at URL=http://www.bestdoctor.com/en/about/why_charge.htm, 1 page, printed Apr. 25, 2002.

Web page, "Geographic Areas Defined," at URL=http://www.checkbook.org/doctors/areas.cfm, 2 pages, printed Apr. 25, 2002.

Web page, "Specialty Categories," at URL=http://www.checkbook.org/doctors/specialty.efm, 1 page, printed Apr. 25, 2002.

Web page, "Terms and Conditions of Use," at URL=http://www.checkbook.org/doctors/newusersubscribe.fm, 1 page, printed Apr. 25, 2002.

Web page, "Welcome to Guide to Top Doctors," at URL=http://www.checkbook.org/doctors/pageone.efm, 1 page, printed Apr. 25, 2002.

Web page, "Health: Best hospitals," at URL=http://www.usnews.com/usnews/nvcu/health/hosptl/tophosp.htm, 1 page, printed Apr. 25, 2002.

Web page, "Health: Best hospitals: Methodology," at URL=http://www.usnews.com/usnews/nvcu/health/hosptl/methodology.htm. 1 page, printed Apr. 25, 2002.

Web page, "Health: Best hospitals by Metro Area," at URL=http//www.usnews.com/usenews/nvcu/health/hosptl/metro.htm, 10 pages, printed Apr. 25, 2002.

Web page, "Health: Best hospitals: Neurology and neurosurgery," at URL=http://www.usnews.com/usnews/nvcu/health/hosptl/specneur.htm, 1 page, printed Apr. 25, 2002.

Web page, "The Best Doctors in America are at Yale," at URL=http://www.med.yale.edu/yfp/best/, 1 page, printed Apr. 25, 2002.

* cited by examiner

SleepApnea.html * USA/Canada * Institutions

SleepApnea > The World > USA/Canada

| Institutions | ⇕ | in USA/Canada | ⇕ | sorted by score | ⇕ | Go |

Output format: ● List   ○ List+   ○ Tree   [ show 10 max ⇕ ]

▬▬▬ Stanford University
▬▬▬ University of Pennsylvania
 ▬▬ Case Western Reserve University
 ▬▬ Louisiana State University
 ▬▬ Johns Hopkins University
 ▬▬ Rutgers University
 ▬▬ Harvard University
 ▬▬ University of Colorado Health Sciences Center
  ▬ Tulane University
  ▬ University of Toronto
▬▬▬ unclassifiable Nashville
▬▬▬▬ <-- Max score for Institutions worldwide.

Home | Search | People | Logout | About us | Comments

*FIG. 7*

SleepApnea.html * USA/Canada * Institutions

SleepApnea > The World > USA/Canada

| Papers | | in USA/Canada | ⇕ | sorted by score | ⇕ | Go |
| People | | | | | | |
| ✓Institutions | ist ○ List+ ○ Tree | show 10 max | ⇕ | | | |
| Cities | | | | | | |
| States/Provinces | University | | | | | |
| Countries | y of Pennsylvania | | | | | |

▬▬▬ Case Western Reserve University
▬▬▬ Louisiana State University
▬▬▬ Johns Hopkins University
▬▬▬ Rutgers University
▬▬▬ Harvard University
▬▬▬ University of Colorado Health Sciences Center
▬▬ Tulane University
▬▬ University of Toronto
▬▬▬ unclassifiable Nashville
▬▬▬▬ <-- Max score for Institutions worldwide.

Home | Search | People | Logout | About us | Comments

*FIG. 8*

SleepApnea.html * USA/Canada * Institutions

SleepApnea > The World > USA/Canada

| Institutions | ⇕ | in the world | sorted by score | ⇕ | Go |
| --- | --- | --- | --- | --- | --- |
| Output format: ⦿ Li | | ✓ in USA/Canada | show 10 max | ⇕ | |
| | | in Britain/Ireland | | | |
| | | in US/UK/Can./Ire. | | | |
| | | outside USA | | | |

▬▬▬ Stanford
▬▬▬ University of Pennsylvania
▬▬ Case Western Reserve University
▬▬ Louisiana State University
▬▬ Johns Hopkins University
▬▬ Rutgers University
▬▬ Harvard University
▬▬ University of Colorado Health Sciences Center
▬ Tulane University
▬▬ University of Toronto
▬▬▬ unclassifiable Nashville
▬▬▬▬ <-- Max score for Institutions worldwide.

Home | Search | People | Logout | About us | Comments

*FIG. 9*

**SleepApnea.html * USA/Canada * Institutions**

SleepApnea > The World > USA/Canada

| Institutions ⇕ | in USA/Canada ⇕ | ✓ sorted by score | Go |
|---|---|---|---|
| | | sorted by name | |
| | | sorted by ZIPcode | |
| | | sorted by distance | |

Output format: ● List   ○ List+   ○ Tre~~e~~

▬▬▬▬ Stanford University
▬▬▬▬ University of Pennsylvania
 ▬▬▬ Case Western Reserve University
 ▬▬▬ Louisiana State University
 ▬▬▬ Johns Hopkins University
  ▬▬ Rutgers University
  ▬▬ Harvard University
  ▬▬ University of Colorado Health Sciences Center
   ▬ Tulane University
   ▬ University of Toronto
▬▬▬ unclassifiable Nashville
▬▬▬▬▬ <-- Max score for Institutions worldwide.

Home | Search | People | Logout | About us | Comments

*FIG. 10*

SleepApnea.html * USA/Canada * Institutions

SleepApnea > The World > USA/Canada

| Institutions ⇕ | in USA/Canada ⇕ | sorted by score ⇕ | Go |

Output format: ● List   ○ List+   ○ Tree   ✓ show 10 max
show 30 max
show 100 max
show all ▬▬▬▬ Stanford University
▬▬▬▬ University of Pennsylvania
▬▬▬ Case Western Reserve University
▬▬▬ Louisiana State University
▬▬▬ Johns Hopkins University
▬▬ Rutgers University
▬▬▬ Harvard University
▬▬▬ University of Colorado Health Sciences Center
▬▬ Tulane University
▬▬ University of Toronto
▬▬▬ unclassifiable Nashville
▬▬▬▬▬ <-- Max score for Institutions worldwide.

Home | Search | People | Logout | About us | Comments

*FIG. 11*

SleepApnea.html * USA/Canada * Cities

SleepApnea > The World > USA/Canada

```
[ Cities      |↕] [ in USA/Canada |↕] [ sorted by score |↕][Go]
Output format: ⦿ List   ○ List+   ○ Tree  [ show 10 max |↕]
```

▬▬▬▬ Boston
▬▬▬▬ Philadelphia
▬▬▬ Palo Alto
▬▬▬ Cleveland
▬▬ Nashville
▬▬ Shreveport
▬▬ Denver
▬▬ Baltimore
▬▬ Newark (NJ)
▬ New Orleans
▬▬▬▬▬ <-- Max score for Cities worldwide.

Home | Search | People | Logout | About us | Comments

*FIG. 12*

SleepApnea.html * USA/Canada * Cities

SleepApnea > The World > USA/Canada

| Cities | ⇕ | in USA/Canada | ⇕ | sorted by score | ⇕ | Go |

Output format: ○ List   ⦿ List+   ○ Tree   [ show 10 max ⇕ ]

▬▬▬▬▬ Boston       [Harvard University * Beth Israel Deaconess Medical Center * New England Medical Center ...]
▬▬▬▬ Philadelphia  [University of Pennsylvania * Thomas Jefferson University * unclassifiable Philadelphia ...]
▬▬▬ Palo Alto      [Stanford University]
▬▬▬ Cleveland      [Case Western Reserve University * Cleveland Clinic * unclassifiable Cleveland ...]
▬▬ Nashville       [Vanderbilt University * unclassifiable Nashville]
▬▬ Shreveport      [Louisiana State University]
▬▬ Denver          [University of Colorado Health Sciences Center * unclassifiable Denver]
▬ Baltimore        [Johns Hopkins University]
▬ Newark (NJ)      [Rutgers University]
▬ New Orleans      [Tulane University * unclassifiable New Orleans]
▬▬▬▬▬▬ <-- Max score for Cities worldwide.

Home | Search | People | Logout | About us | Comments

*FIG. 13*

SleepApnea.html * USA/Canada * Cities

SleepApnea > The World > USA/Canada

| Cities ⇕ | in USA/Canada ⇕ | sorted by score ⇕ | Go |

Output format: ○ List  ○ List+  ● Tree  [ show 10 max ⇕ ]

━━━ Boston
        Harvard University
        Beth Israel Deaconess Medical Center
        New England Medical Center
        Tufts University
        Boston University
━━━ Philadelphia
        University of Pennsylvania
        Thomas Jefferson University
        unclassifiable Philadelphia
━━━ Palo Alto
        Stanford University
━━━ Cleveland
        Case Western Reserve University
        Cleveland Clinic
        unclassifiable Cleveland
━━━ Nashville
        Vanderbilt University
        unclassifiable Nashville
        *{ FIVE CITIES NOT SHOWN }*
━━━━━━ <-- Max score for Cities worldwide.

Home | Search | People | Logout | About us | Comments

FIG. 14

SleepApnea.html * USA/Canada * States/Provinces

SleepApnea > The World > USA/Canada

[ States/Provinces ◆ ] [ in USA/Canada ◆ ] [ sorted by score ◆ ] [ Go ]
Output format: ○ List   ● List+   ○ Tree   [ show 10 max ◆ ]

| | | |
|---|---|---|
| ▬▬▬▬ | California | [Palo Alto * San Diego * Los Angeles ...] |
| ▬▬▬▬ | Pennsylvania | [Philadelphia * Hershey (PA) * Pittsburgh ...] |
| ▬▬▬ | Ohio | [Cleveland * Cincinnati * Toledo ...] |
| ▬▬▬ | Lousiana | [Shreveport * New Orleans] |
| ▬▬▬ | Massachusetts | [Boston] |
| ▬▬ | Tennessee | [Nashville * Memphis] |
| ▬▬ | New York | [New York City * Albany * Stony Brook (NY) ...] |
| ▬▬ | Maryland | [Baltimore * Bethesda] |
| ▬ | Ontario | [Toronto * London (ON) * unclassifiable Ontario ...] |
| ▬ | Colorado | [Denver * unclassifiable Colorado] |
| ▬▬▬ | unclassifiable USA | |
| ▬▬▬▬▬ | <-- Max score for States/Provinces worldwide. | |

Home | Search | People | Logout | About us | Comments

*FIG. 15*

SleepApnea.html * USA/Canada * States/Provinces

SleepApnea > The World > USA/Canada

```
[ States/Provinces | ≑ ] [ in USA/Canada | ≑ ] [ sorted by score | ≑ ] [ Go ]
Output format: ○ List   ○ List+   ● Tree   [ show 10 max | ≑ ]
```

▬▬▬▬ California
    Palo Alto
        Stanford University
    San Diego
        University of California San Diego
        unclassifiable San Diego
    Los Angeles
        University of California Los Angeles
        University of Southern California
        University of California Irvine
        unclassifiable Los Angeles
    Oakland
    San Francisco
        University of California San Francisco
    San Jose
    unclassifiable California
    *{ NINE STATES AND PROVINCES NOT SHOWN }*
▬▬▬▬ unclassifiable USA

▬▬▬▬ <-- Max score for States/Provinces worldwide.

Home | Search | People | Logout | About us | Comments

*FIG. 16*

SleepApnea.html * in Stanford University * People

SleepApnea > The World > USA > California > Palo Alto > in Stanford University   http://www.stanford.edu

| People ⇕ | in Stanford University ⇕ | sorted by score ⇕ | Go |

Output format: ○ List   ⦿ List+   ○ Tree   [ show 10 max ⇕ ]

People 1-10 ° 1-10 ° 11-20 ° 21-30 ° 31-40

▬▬▬▬▬ Guilleminault C ◘   [Stanford University ° Palo Alto ° California ° USA] [USA]

▬▬ Li KK ◘   ? [USA] [Stanford University ° Palo Alto ° California ° USA]

▬▬ Riley RW ◘   ? [Stanford University ° Palo Alto ° California ° USA] [USA]

▬▬ Powell NB ◘   ? [Stanford University ° Palo Alto ° California ° USA] [USA]

▬▬ Pelayo R ◘   [Stanford University ° Palo Alto ° California ° USA]

▬ Troell RJ ◘   ? [Stanford University ° Palo Alto ° California ° USA]

▬ Terris DJ ◘   [Stanford University ° Palo Alto ° California ° USA]

▬ Li K ◘   [Stanford University ° Palo Alto ° California ° USA]

▪ Troell R ◘   ? [USA] [Stanford University ° Palo Alto ° California ° USA]

▪ Messner AH ◘   [Stanford University ° Palo Alto ° California ° USA] [San Jose ° California ° USA]

▬▬▬▬▬ <-- Max score for a person worldwide.

Home | Search | People | Logout | About us | Comments

FIG. 17

SleepApnea.html * Pelayo R * Papers

SleepApnea > The World > USA > California > Palo Alto > Stanford University > Pelayo R

[ Papers ≑ ] [ of Pelayo R ≑ ] [ sorted by score ≑ ] [Go]
Output format: ○ List  ● List+  ○ Tree  [ show 10 max ≑ ]

Pelayo R
Location(s):
- Stanford University ° Palo Alto ° California ° USA

Possible email address(es):
- PELAYO@LELAND.STANFORD.EDU

Co-authors, with number of co-authored papers:
Guilleminault C ■ (3) ° Messner AH ■ (1) ° Tsutumi M ■ (1) ° Horita M ■ (1) ° Kim YD ■ (1)

---

Papers: { *TWO PAPERS NOT SHOWN* }

■ Sleep-disordered breathing in children. (1998.08) ■

Pelayo R ■   Guilleminault C ■

Stanford Sleep Disorders Center, CA 94305, USA.
pelayo@leland.stanford.edu

[ Stanford University ° Palo Alto ° California ° USA ]

---

■ Pediatric sleep-related breathing disorders. (2000.03) ■

Pelayo R ■   Messner AH ■

Department of Surgery, Stanford University, Lucile Salter Packard Children's Hospital, Palo Alto, CA 94304, USA.

[ Stanford University ° Palo Alto ° California ° USA ]

---

████████ <-- Max score for a paper worldwide.

Home | Search | People | Logout | About us | Comments

*FIG. 18*

SleepApnea.html * The world * Countries

SleepApnea > The World > The world

| Countries | ♦ | in the world | ♦ | sorted by score | ♦ | Go |

Output format: ○ List   ● List+   ○ Tree   [ show 10 max | ♦ ]

▬▬▬▬ USA             [California * Pennsylvania * Ohio ...]
       ▪ United Kingdom [London (EN) * Edinburgh * Oxford (EN) ...]
       ▪ Canada         [Ontario * Quebec * Manitoba ...]
       ▪ Japan
       ▪ Australia
       ▪ Germany
       ▪ France
       ▪ Sweden
       ▪ Italy
       ▪ Finland
▬▬▬▬▬▬ unclassifiable The World
▬▬▬▬ <-- Max score for Countries worldwide.

Home | Search | People | Logout | About us | Comments

*FIG. 19*

SleepApnea.html * The world * People

SleepApnea > The World > The world

| People | ⇕ | in the world | ⇕ | sorted by score | ⇕ | Go |

Output format: ○ List   ● List+   ○ Tree   [ show 10 max | ⇕ ]

People 1-10 ° 1-10 ° 11-20 ° 21-30 ° 31-2596

▬▬▬▬ Guilleminault C ▪  [Stanford University ° Palo Alto ° California ° USA] [USA]

▬▬▬ Cherniack NS ▪  [Rutgers University ° Newark (NJ) ° New Jersey ° USA]

▬▬ Douglas NJ ▪  [University of Edinburgh ° Edinburgh ° United Kingdom] [Finland]

▬ McNicholas WT ▪  [Dublin ° Ireland]

▬ Strohl KP ▪  [Case Western Reserve University ° Cleveland ° Ohio ° USA] [New York University ° New York City ° New York ° USA]

▬ Millman RP ▪  [Brown University ° Providence ° Rhode Island ° USA]

▬ Pepin JL ▪  ? [France] [United Kingdom]

▬ Somers VK ▪  [University of Iowa ° Iowa City ° Iowa ° USA]

▬ Levy P ▪  [France]

▬ Punjabi NM ▪  ? [Johns Hopkins University ° Baltimore ° Maryland ° USA]

▬▬▬▬▬ <-- Max score for a person worldwide.

Home | Search | People | Logout | About us | Comments

*FIG. 20*

METHOD AND SYSTEM FOR IDENTIFYING EXPERTISE

CROSS REFERENCES TO RELATED APPLICATIONS

This application claims priority to U.S. Provisional Application No. 60/230,689, filed on Sep. 7, 2000, entitled "METHOD AND SYSTEM FOR IDENTIFYING EXPERTISE", which is herein incorporated by reference in its entirety for all purposes.

COPYRIGHT NOTICE

A portion of the disclosure recited in the specification contains material which is subject to copyright protection. Specifically, a source code appendix is included that lists instructions for a process by which the invention is practiced in a computer system. The copyright owner has no objection to the facsimile reproduction of the specification as filed in the Patent and Trademark Office. Otherwise, all copyright rights are reserved. This source code appendix is herein incorporated by reference in its entirety for all purposes.

BACKGROUND OF THE INVENTION

The present invention generally relates to knowledge acquisition. More particularly, the invention provides a method for web based searching of a database or databases in the health care field. The database can be selected from custom or commercial databases, e.g., the U.S. Government's Medline database of scientific articles (hereinafter "Medline").

Conventional ways of finding desirable hospitals and doctors are very limiting. For example, most doctors, who specialize in a selected area of practice, are often uncovered by a referral, which is generally word of mouth from one person to another person. Most often, such word of mouth is from a family member, co-worker or the like. Similarly, a desirable hospital is often found through a referral mechanism, as well. Depending upon such referral, doctor and/or hospital quality has been difficult to control. So, consumers do not presently have a reliable, objective method to find a desirable doctor and/or health care providers.

There have been some attempts to uncover experts in the healthcare field through printed documents. Such printed documents include, among others, periodicals, etc. To identify such experts in a field who may be able to comment on breaking health news stories, consumers must often conduct extensive research or use limited, non-objective printed guides. Similarly, other professionals in the field such as the media also need to perform extensive research and the like to find such breaking heath news stories. Still further, makers of healthcare policy and reimbursement programs desire methods to identify centers of excellence around which specialized health care services could be consolidated. Accordingly, it is often difficult to uncover such experts in the healthcare field using conventional techniques.

From the above, it is seen that a technique for improving access to information is highly desirable.

SUMMARY OF THE INVENTION

According to the present invention, a technique including a method and system for identifying an entity with an expertise is provided. In an example, the invention provides a method for web based searching of a database or databases in the health care field. The database can be selected from custom or commercial databases, e.g., Medline, etc.

In a specific embodiment, the invention provides a method of identifying entities having expertise in one or more subjects. Among other features, the method includes querying a database for documents (e.g., articles, papers, periodicals) relevant to a subject; and calculating a first score for each relevant document. The method also identifies entities affiliated with one or more relevant documents; and calculates a second score for each entity based on the one or more first scores of the one or more relevant documents affiliated with the entity. A step of ranking expertise of the entities based on the respective second scores of the entities is included.

In an alternative embodiment, the invention provides a system for identifying expertise in a subject. The system has a server system coupled with a database of documents. The server system has a memory with a variety of computer codes. The codes include a first code configured to receive a subject from a user; and a second code configured to query the database for documents relevant to the subject. The memory also has a third code configured to calculate a score for each relevant document; and a fourth code configured to identify entities affiliated with one or more of the relevant documents. A fifth code is configured to calculate a score for each entity based on the one or more scores of the one or more relevant documents affiliated with the entity. A sixth code is configured to provide to the user a ranking of the expertise of the entities based on the respective scores of the entities. Depending upon the embodiment, the invention can also include only some of the codes above, as well as other codes, which can implement the functionality described herein.

Numerous benefits are achieved by way of the present invention. In a specific embodiment, the invention can be implemented using conventional hardware and/or software. In other aspects, the invention can be used to find a leading expert in a particular health care field. The invention can also be used to find a leading hospital for a particular health care field. Still further, the invention can be used to uncover almost any entity, which is desirable for a particular field. Geographical areas can also be uncovered for particular expertise. In most embodiments, the invention is easy to use and can be implemented on a computer network, such as a local area network, a wide area network, a world wide area network, any combination of these, and the like. Depending upon the embodiment, one or more of these benefits may be achieved. These and other benefits are provided in more detail throughout the present specification and more particularly below.

These and other embodiments of the present invention, as well as its advantages and features are described in more detail in conjunction with the text below and attached.

BRIEF DESCRIPTION OF THE DRAWINGS

FIGS. 4-20 illustrate examples of web pages that may be used to implement methods according to various embodiments of the invention

DESCRIPTION OF THE SPECIFIC EMBODIMENTS

System Overview

Figure 1:
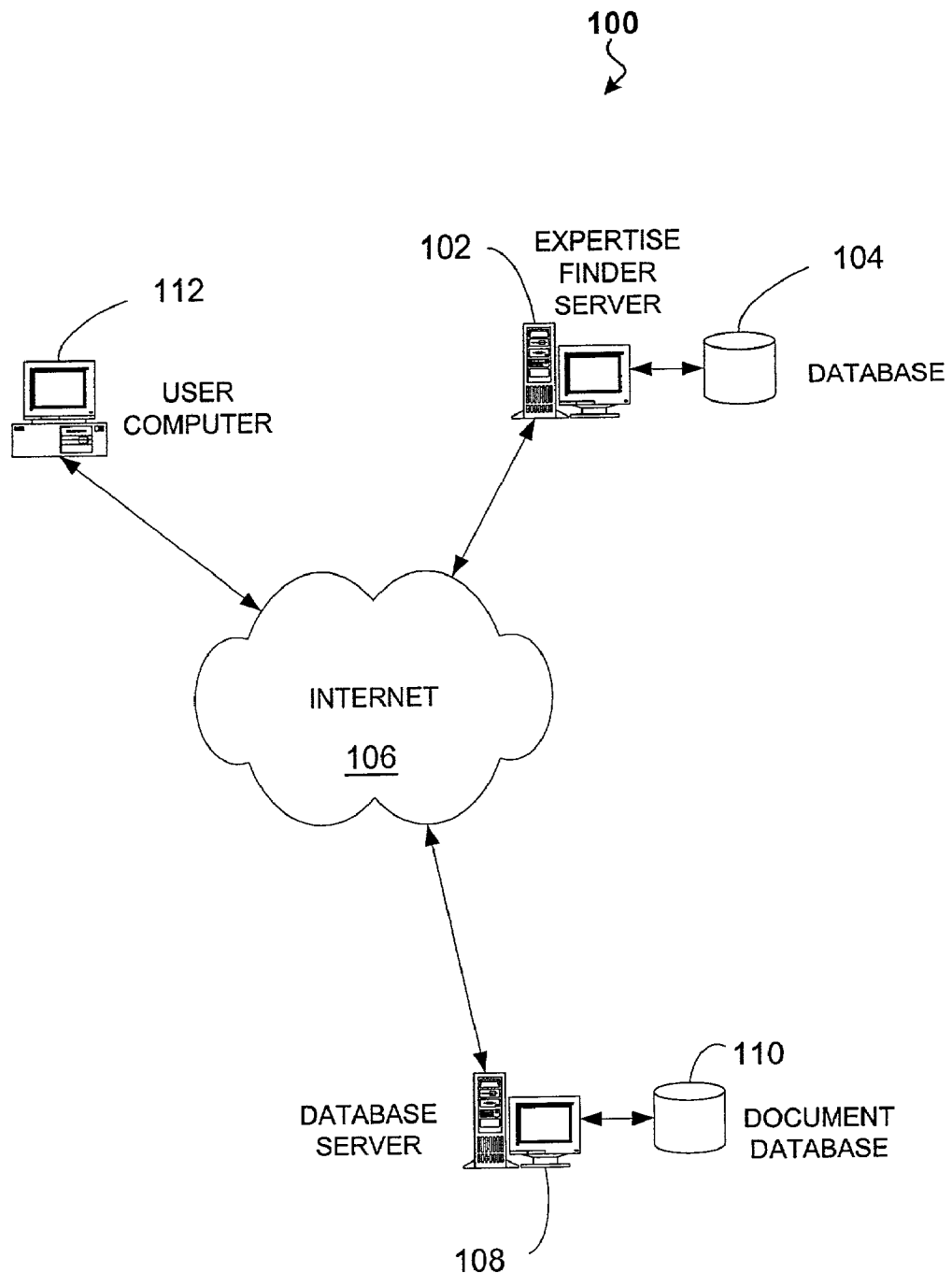
FIG. 1 is a simplified block diagram of an environment in which methods according to various embodiments of the invention may be implemented.

FIG. 1 is a simplified block diagram of an environment in which methods according to various embodiments of the invention may be implemented. This diagram is merely for illustrative purposes and is not intended to limit the scope of the claims herein. An expertise finder server system 102 is coupled with a database 104 and a network 106. Additionally, a database server system 108 is coupled with a database 110 of documents and the network 106. Additionally, a user computer 112 is coupled with the network 106.

Network 106 allows the expertise finder server system 102, the database server system 108, and the user computer 112 to communicate with other computers and with each other. The network 106 may be a local area network, a wide area network, an internet, the Internet, an intranet, an extranet, or the like.

The expertise server system 102 may be coupled to the network 106 via a relatively high bandwidth transmission medium such as a T1 or T3 line. With respect to the electronic database 104, it generally contains WebPages, forms, etc. The database 104 can be composed of a number of different databases. These databases can be located in one central repository, or alternatively, they can be dispersed among various distinct physical locations. These databases can be categorized and structured in various ways based on the needs and criteria of the database designer. Methods used to create and organize databases are commonly known in the art, for example, relational database techniques can be used to logically connect these databases. Database 104 can be a relational database, distributed database, object-oriented database, mixed object-oriented database, or the like. Database products with which the present invention may be implemented include, but are not limited to, IBM's DB2, Microsoft's Access and FoxPro, and database products from Oracle, Sybase, and Computer Associates.

In one embodiment, the database or databases 104 can be physically located separate from the expertise finder server system 102. These databases can reside on remote, distant servers on a local area network or the Internet. Under this arrangement, whenever any data are needed, the processor needs to access the necessary database(s) via a communication channel to retrieve the requisite data for analysis. For example, the processor can access and retrieve data from a remote database via a computer network such as a LAN or the Internet. Generally, the expertise server system 102 and database 104 store information and disseminate it to individual computers e.g. 112 over the network 106.

The database server system 108 may also be coupled to the network 106 via a relatively high bandwidth transmission medium such as a T1 or T3 line. With respect to the electronic database 110, it generally contains electronic versions of documents such as, for example, technical articles and papers, in fields such as medicine, genetics, physics, chemistry, engineering, law, and the like. The database 110 can also include legal cases. As discussed with respect to the database 104, the database 110 can comprise a number of different databases. In one embodiment, the database 110 is the Medline database. It is to be understood that other databases may be used instead of, or in conjunction with, Medline, such as other Medlars databases, the Science Citation Index, Medlex, Westlaw, Lexis, Dialog, and the like.

In some embodiments, the expertise server system 102 and the database server system 108 are the same server system, whereas in other embodiments, the two server systems are separate. Similarly, in some embodiments, the database 104 and the document database 110 are included in one database system, whereas in other embodiments, the two databases are separate.

The user computer 112 may be configured with many different hardware components and can be made in many dimensions, styles and locations (e.g., laptop, palmtop, pentop, server, workstation and mainframe). The user computer 112 may be, as one example, a conventional desktop personal computer or workstation having the ability to connect to network 106 and being capable of running customized software supporting the service provided by the present invention. In some embodiments, user computer 112 includes web browsing software, or the like for interacting with expertise finder server system 102. In a specific embodiment, the network 106 is the Internet, and the expertise server system 102 provides Web Pages to computers, such as user computer 112, via the Internet 106.

Figure 2:
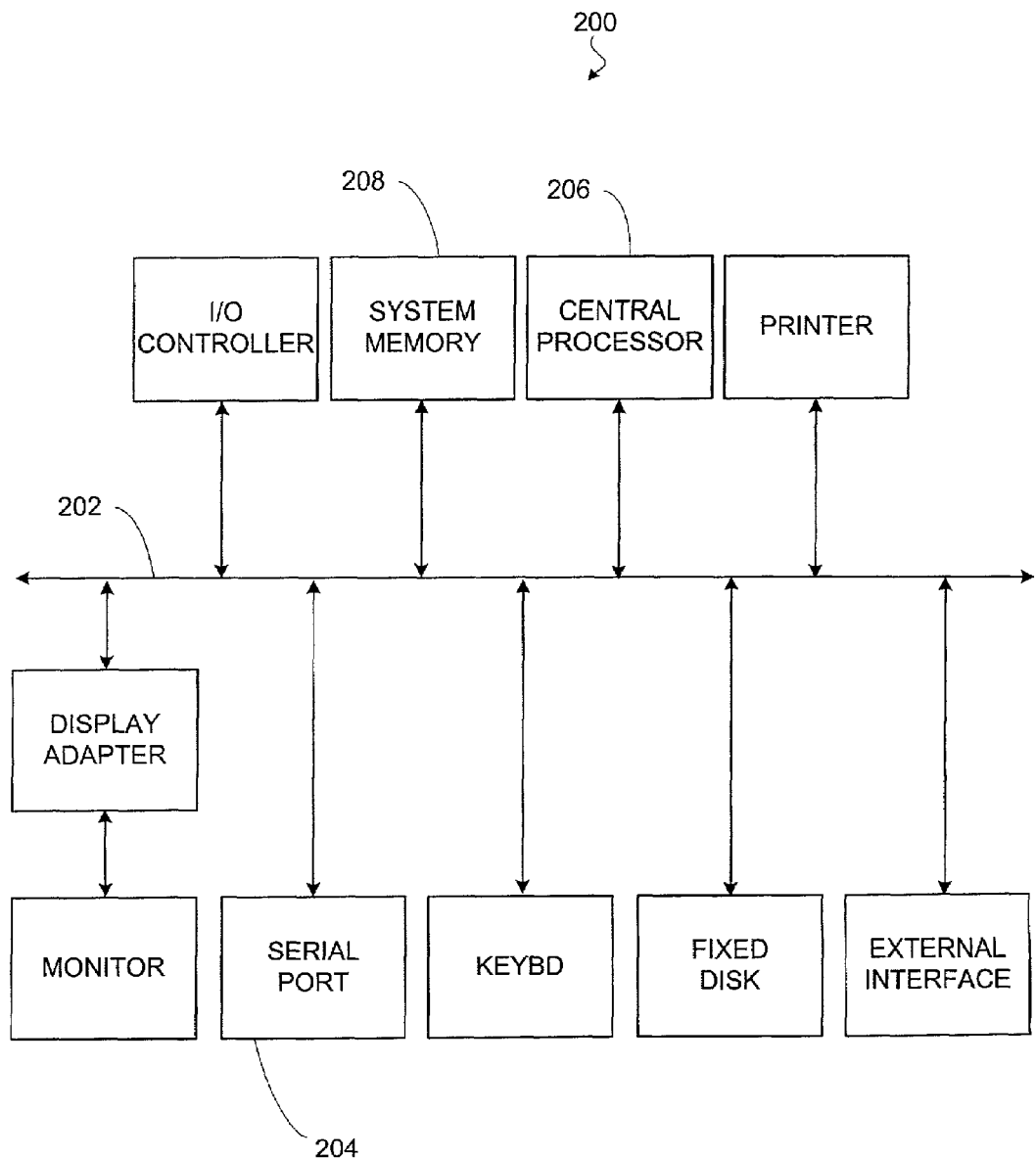
FIG. 2 is a simplified block diagram of basic subsystems in a representative computer system in which methods according to various embodiments of the invention may be implemented.

Embodiments according to the present invention can be implemented in a single application program, or can be implemented as multiple programs in a distributed computing environment, such as a workstation, personal computer or a remote terminal in a client server relationship. FIG. 2 illustrates basic subsystems in a representative computer system in which methods according to various embodiments of the invention may be implemented. In these embodiments, each of user computers 112, expertise finder server system 102, and/or database server system 108 may comprise one or more of computer systems 200 or the like. This diagram is merely an illustration and should not limit the scope of the claims herein. One of ordinary skill in the art will recognize other variations, modifications, and alternatives In certain embodiments, the subsystems are interconnected via a system bus 202. Additional subsystems such as a printer, keyboard, fixed disk and others are shown. Peripherals and input/output (I/O) devices can be connected to the computer system by any number of means known in the art, such as serial port 204. For example, serial port 204 can be used to connect the computer system to a modem, which in turn connects to a wide area network such as the Internet, a mouse input device, or a scanner. The interconnection via system bus 202 allows central processor 206 to communicate with each subsystem and to control the execution of instructions from system memory 208 or the fixed disk, as well as the exchange of information between subsystems. Other arrangements of subsystems and interconnections are readily achievable by those of ordinary skill in the art. System memory 208, and the fixed disk are examples of tangible media for storage of computer programs, other types of tangible media include floppy disks, removable hard disks, optical storage media such as CD-ROMS and bar codes, and semiconductor memories such as flash memory, read-only-memories (ROM), and battery backed memory.

Finding Expertise

The invention will now be discussed in the context of medical expertise. However, it is to be understood that the present invention is not limited to identifying medical expertise. On the contrary, the present invention may be used to identify expertise in many different fields such as healthcare, genetics, physics, chemistry, engineering, law, and the like.

Figure 3:
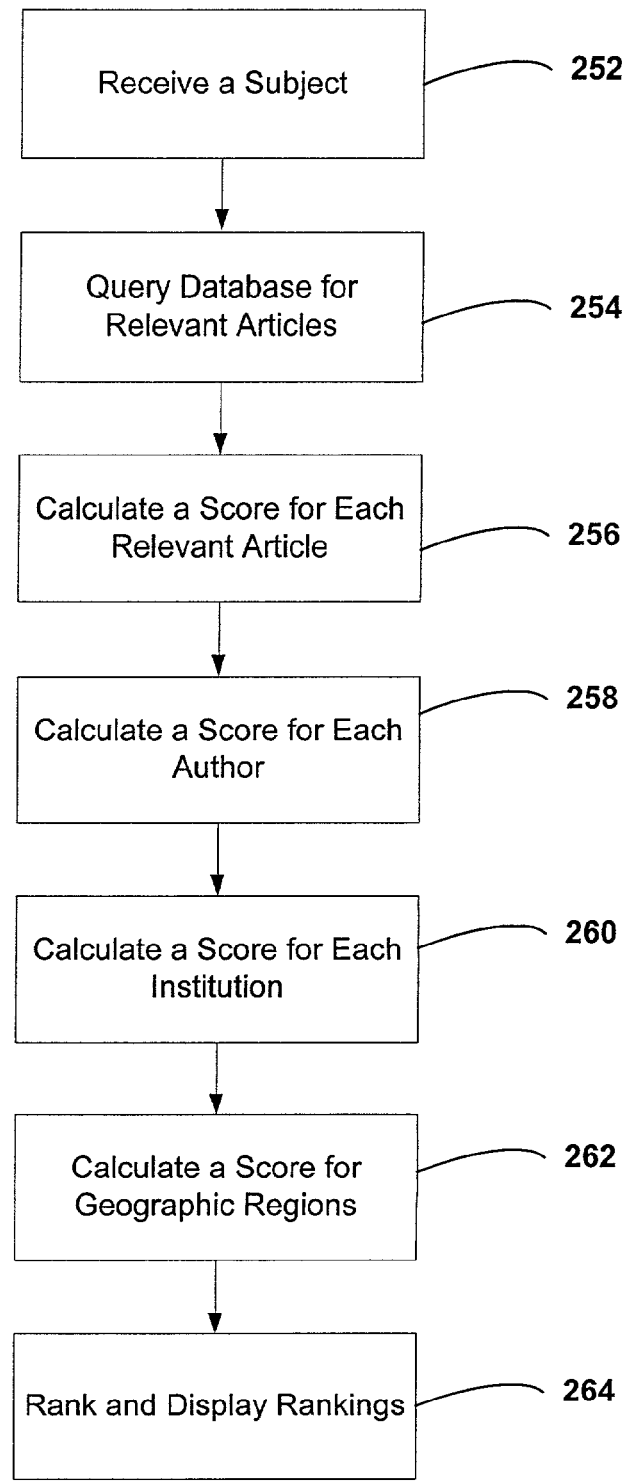
FIG. 3 is a simplified flow diagram of a method according to one embodiment of the invention.

FIG. 3 is a simplified flow diagram of a method according to one embodiment of the invention. This diagram is merely for illustrative purposes and is not intended to limit the scope of the claims herein. The flow illustrated in FIG. 3 may be implemented, for example, on a system such as the system 100 shown in FIG. 1. In a step 252, a subject for which a user desires to identify expertise is received. In some embodiments, the subject may be received via a world wide network of computers such as the Internet, or the like. Referring to FIG. 1, in a specific embodiment, the user computer 112 transfers a subject to the expertise server system 102 via the Internet.

Then, in a step 254, a database is queried to find documents relevant to the subject. In a specific embodiment, the expertise server system 102 queries the database 110 via the Internet and via the database server system 108.

After receiving a response to the database query, a score is calculated, in a step 256, for each document identified as relevant to the subject. In a specific embodiment in which the Medline database is queried, a document that is a review article is given more points than an article that is not a review article. Additionally, different types of review articles are awarded different point amounts.

Then, in a step 258, a score is calculated for each author identified as an author of one or more of the relevant documents. In one embodiment, the score of an author is based on the scores of documents authored by the author. In another embodiment, the author's score is additionally based on, for each document, the position of the author's name with respect to other authors.

In a step 260, a score may be calculated for institutions affiliated with the documents. In one embodiment, a score for an institution is calculated based on the scores of documents that emanate from the institution. In another embodiment, the score is based on the scores of authors affiliated with the institution. Similarly, in a step 262, a score may be calculated for geographic areas. In one embodiment, a score for a geographic area is calculated based on the scores of documents that emanate from the institutions in the geographical area. In another embodiment, the score is based on the scores of authors associated with the geographic area. Then, in a step 264, the scores of one or more of the documents, authors, institutions, and geographic areas are ranked and the one or more corresponding rankings are provided to the user.

One skilled in the art will recognize many variations, modifications, and alternatives to the flow of FIG. 3. For instance, in some embodiments only one of steps 258, 260 and 262 are performed. In other embodiments, any two of steps 258, 260 and 262 are performed.

Querying the Database

As described above, a database of documents is queried for documents relevant to a subject of interest. In some embodiments, the query is determined such that documents relevant to the subject of interest, but not necessarily relevant to determining expertise, will be excluded. For example, in the context of finding medical expertise, the query could be determined such that letters to the editor will be excluded. Also, in the context of finding clinical care expertise, the query could be determined such that documents that do not deal with humans will be excluded.

In some embodiments, the query is determined such that synonyms of the subject provided by the user are also included in the query. For example, a user may provide the subject "kidney disease," and a query could be determined that included "renal disease." In a specific embodiment, a database of synonyms is coupled to expertise finder server system 102. The database of synonyms can be included in database 104, or in a separate database. In this embodiment, upon receiving a subject from the user, the database of synonyms is queried to determine whether any synonyms should be included in the query of document database 110.

In one specific embodiment, the query of document database 110 limits documents to those from the most recent ten years. In some other embodiments, the query may limit to some other number of years (e.g., 5, 15, etc.). In yet other embodiments, the query does not include such a time limit.

One skilled in the art will recognize many other variations and alternatives. For instance, queries can be optimized based on the particular subject. For example, a query for a search for expertise related to the diagnosis of disease can be determined according to one optimization, whereas a query for a search for surgical expertise can be determined according to another optimization.

Scoring Documents

In embodiments according the invention, scores for documents are calculated based on information transmitted from the database server 108 to the expertise finder server 102 in response to a query. In some embodiments, the expertise finder server 102 receives a document record for each of one or more documents in response to the query. Each document record includes one or more data fields. For example, the Medline database includes the following fields: TITLE, AUTHOR, ADDRESS, DATE PUBLISHED, and PUBLICATION TYPE.

In these embodiments, a score for a document is calculated based on information returned in the data fields. For example, a point value can be assigned to each of a plurality of data fields for a document, and then the point values summed to calculate the score for the document. The point value assigned to a particular data field can be determined by the information returned in that data field.

For instance, in some embodiments, a data field may indicate the type of document, and a score assigned to the type of document based on the information provided in this data field. In a specific embodiment, a higher point value is assigned to review articles than non-review articles. And, in another specific embodiment, some types of review articles are assigned point values than other types of review articles.

One particular simplified example of an algorithm for scoring a document from the Medline database is provided. In this example, if the PUBLICATION TYPE data field has value REVIEW or PRACTICE GUIDELINE, the document is given 10 points. If the PUBLICATION TYPE data field has value LETTER, the document is assigned 0 points. Otherwise, the document is assigned 1 point. Additionally, the document's score can be adjusted according to when it was published. For example, if the DATE PUBLISHED field indicates that the document was published within the last 3 years, then the document score is increased by 5 points. The above example is merely an illustration of one of the many ways in which a document may be scored. Additionally, further details are provided in the attached Appendix. One skilled in the art will recognize many other equivalents, modifications, and alternatives. For example, the same scoring algorithm need not be used for each search. Different scoring algorithm can be used, for example, according to the particular database queried, the particular subject, the number of document records returned by the query, etc.

In other embodiments, some of the optimizations related to the query described above can be implemented in the scoring algorithm rather than in determining the query. For example, a letter to the editor, a paper that does not consider humans, etc. can be assigned a score of zero.

In some embodiments, a scoring algorithm can vary according to the number of documents that were returned by the query. For example, in the context of finding medical expertise, it has been found that when only a few documents are returned, the type of document (review article or whatever) is less informative. Thus, when the number of documents returned are low, the data field related to the type of document can be assigned a same point value, regardless of the information returned in this data field. In one specific example, the point value assigned is zero.

In other embodiments, the score of a document can be adjusted based on the type of publication in which it appeared. For instance, some publications, journals, etc., may be more highly regarded than others. This has been quantified in various ways. For example, the Institute for Scientific Information assigns an "impact factor" to scientific journals. Thus, in some embodiments, the "impact factor" assigned to the journal can be used to adjust the score of the document.

Scoring Authors

In some embodiments according to the invention, scores for authors are calculated. In some of these embodiments, a score for an author is calculated based on the score of each document returned of which he/she is an author. In one specific embodiment, the score for an author is the sum of the scores of the documents of which he/she is an author. In other embodiments, the score for an author is a weighted sum of the scores of the documents of which he/she is an author. For example, a higher weight may be assigned to a document if the author is the first listed than when the author is not the first listed. Similarly, in some embodiments, a higher weight may be assigned to a document if the author is the "corresponding author" (i.e. the author to whom correspondence is addressed). In other embodiments, an author's score may be increased by an increment for each document of which he/she is first listed or a corresponding author. In one specific embodiment in which the Medline database is queried, the corresponding author of a document is determined by examining the email address often attached to a document's ADDRESS field.

Scoring Institutions/Geographic Areas

In some embodiments according to the invention, scores for institutions are calculated. In some of these embodiments, a score for an institution is calculated based on the score of each document that emanated from that institution. In one specific embodiment, the score for an institution is the sum of the scores of the documents that emanated from that institution. In other embodiments, the score for an institution is a weighted sum of the scores of the documents that emanated from that institution.

Some databases may include a data field that indicates from which institution or institutions the document emanated. In other databases, such a field may not be included. For example, the Medline database sometimes, but not always, provides the institutional affiliation of the first author in the ADDRESS field. Thus, one of the institutions from which the document emanated can be assumed to be the institution found in the ADDRESS field.

With the Medline database, there is no standard nomenclature for institutions and there is no standard syntax for the contents of the ADDRESS field. Thus, in one particular embodiment in which the Medline database is searched, a plurality of heuristics are employed to parse the contents of the ADDRESS field and compare to a database of institutions.

The above-described embodiment provides a method for determining the institution with which the first author of a document is affiliated. In one particular embodiment, it is assumed that the other authors (if any) are affiliated with the same institution. In other embodiments, determining the one or more institutions from which a document emanated can include heuristics that examine, for example, any or all of: (a) clustering of authors on a plurality of papers, (b) institutional affiliations of the author when the author is the first author, and (c) temporal variations in imputed institutional affiliations.

Similarly, in some embodiments according to the invention, scores for geographic areas are calculated. In some of these embodiments, a score for a geographic area is calculated based on the score of each document that emanated from that geographic area. In one specific embodiment, the score for a geographic area is the sum of the scores of the documents that emanated from that geographic area. In other embodiments, the score for a geographic area is a weighted sum of the scores of the documents that emanated from that geographic area.

In some embodiments, from which geographic region(s) a particular document emanated can be determined based on the determination of the institution(s) from which the document emanated. For example, if it is determined that a particular document emanated from Johns Hopkins, then it can be determined that document emanated from Baltimore, Md. In other embodiments, from which geographic region(s) a particular document emanated can be determined by examination of data fields returned by the query. For example, in embodiments that query the Medline database, the ADDRESS field can be examined to determine a geographic area.

In some embodiments, the score of an institution or geographic area is determined based on the scores of the authors affiliated with the institution or geographic area. In a specific embodiment, the determination of the score of an institution or geographic area includes employing a normalization factor that modifies the effect of having multiple authors on the same document from the same institution or geographic region.

In one specific embodiment in which the Medline database is queried, an ADDRESS field that is returned for a document is parsed into a structured geographic representation. Unlike most of the Medline data fields, the ADDRESS field is natural language text. In this specific embodiment, tokenizing rules and heuristics, as well as a database, are employed to identify institutions and geographical entities within the field. For example, an email address is examined and it is determined that the author is from Greece when the author's email address ends in ".gr". Similarly, it is determined that the author of a document is affiliated with Harvard University when "Children's Hospital" appears in a Boston address line. Also, it is determined that the author of a document is affiliated with the University of Pennsylvania when "Children's Hospital" appears in a Philadelphia address.

Displaying Rankings

In some embodiments, expertise scores of authors, institutions, geographic areas are represented with score bars. Depending upon the particular algorithm used for calculating expertise scores, the point scale may be arbitrary. Thus, the absolute numbers of the expertise scores are less useful than the relative scores. In some embodiments, expertise scores are provided to the user as bars. For example, the longer the bar, the greater the expertise. In a specific embodiment, a normalizing bar is provided on the display of expertise scores. For example, it has been discovered that Palo Alto is the world's city with the greatest expertise in sleep apnea. So, if a user desires to view the levels of expertise for various cities in Ohio, for example, the Palo Alto scoring bar is additionally displayed, so that the user can compare how the Ohio expertise scores compare with the highest score, Palo Alto.

User Interface

Figure 4:
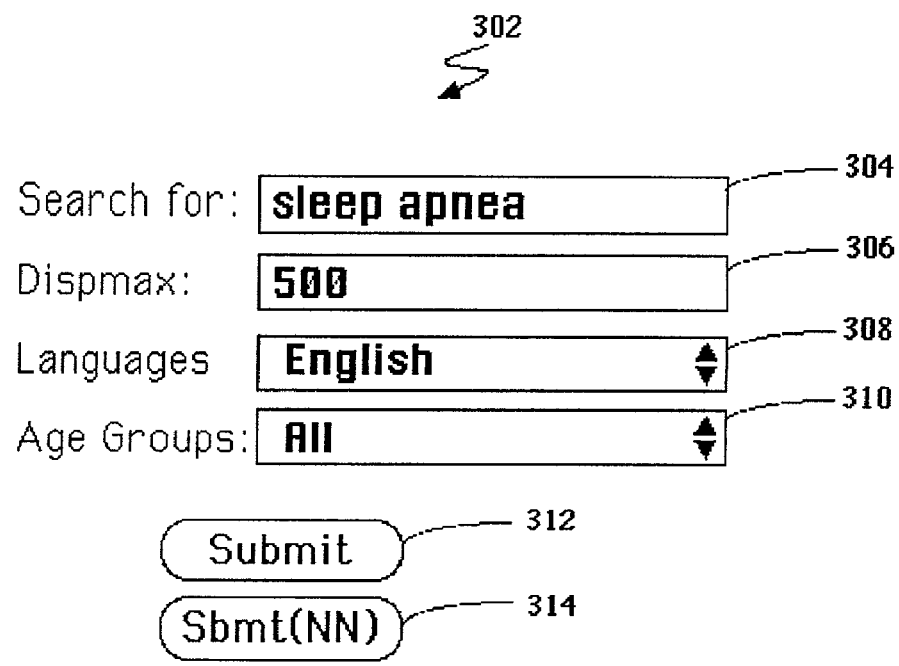
Figure 5:
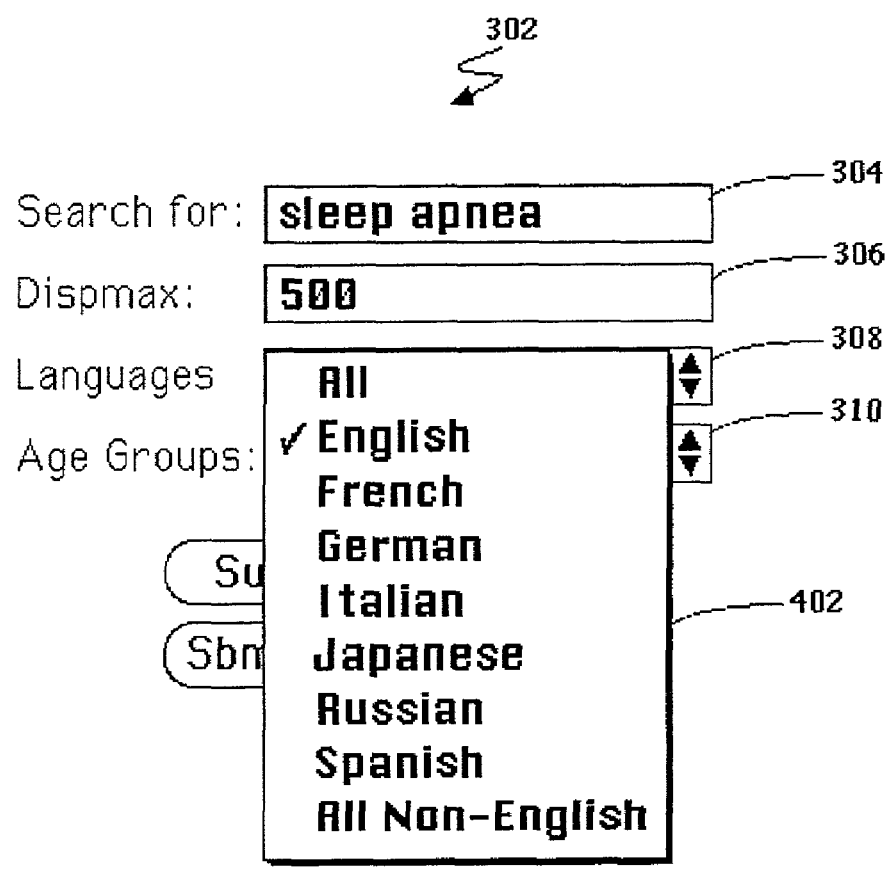
Figure 6:
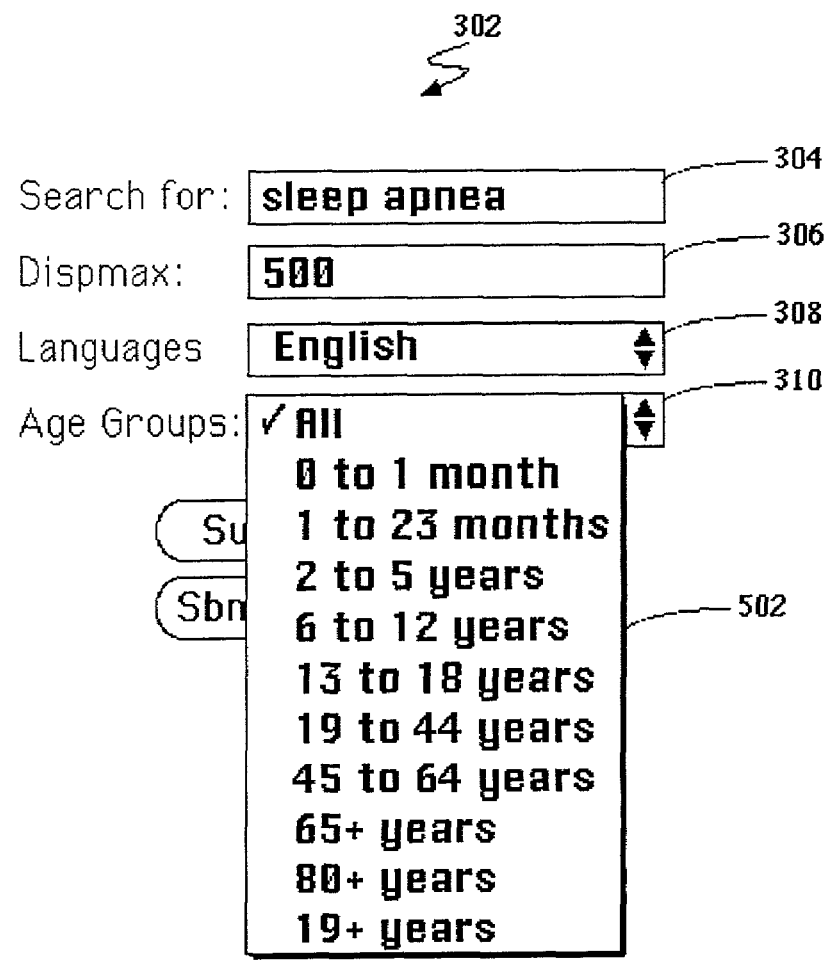

FIGS. 4-20 illustrate examples of web pages that can be used to implement one embodiment according to the invention. For instance, FIGS. 4-6 illustrate an example of a web page form 302 for providing a subject for which a user desires to identify expertise. The form 302 includes user interface components well known to those skilled in the art, including type-in boxes 304 and 306, selectable menus 308 and 310, and submit buttons 312 and 314. Examples of drop-down menus are illustrated in FIGS. 5 and 6.

FIG. 7 and FIGS. 12-20 illustrate various examples of displaying expertise rankings to a user. FIGS. 8-11 illustrate examples of drop-down menus for selecting display-options for expertise rankings. The examples illustrate one embodiment that provides a user interface that permits a user to choose a desired level of geographic detail.

Variations

In some embodiments, when a document cannot be classified in full geographical detail (down to the level of institution), it is assigned into an "unclassified" bucket. For example, parsing the document's ADDRESS field may show it emanated from Cleveland, but the institution is unknown. The document is classified as "unclassified Cleveland". As another example, if a document emanated from Michigan, but the city and institution are unknown, the document is classified as "unclassified Michigan".

In some embodiments, a particular person, institution, etc., is determined as affiliated with a document if there is an exact match of the name of the person, institution, etc., with the document (e.g., within a data field returned in response to a query). In other embodiments, such a determination can be made also when the name is not an exact match, but similar (e.g., J. Sotos and J. G. Sotos). In a particular embodiment, rules for determining whether similar names refer to the same author, institution, etc., takes into account that common names, such as, for example, J Smith and J G Smith, can less reliably be assumed the same.

Although the Medline ADDRESS field is supposed to contain data about the first author of a paper, sometimes another author's email address is given in the ADDRESS field. In the future, it would make sense for the system to try matching the email address in the ADDRESS field with the author to which it properly belongs.

To prove the principle and operation of the present invention, we implemented aspects of the invention using computer source code. As merely an example, the computer source code is provided in the Appendix, which is incorporated by reference. The source code was prepared in HTML/Javascript and Macintosh Common Lisp., which is not intended to be limiting in any manner. Here, one of ordinary skill in the art would recognize many other variations, alternatives and modifications. The present code can be implemented in the hardware described herein, as well as others. It could also be distributed or even implemented solely in hardware. The functionality of the source code can be further combined or even separated.

Numerous benefits are achieved by way of the present invention. Embodiments of the invention can be implemented using conventional hardware and/or software. In other aspects, embodiments of the invention can be used to find a leading expert in a particular health care field. Embodiments of the invention can also be used to find a leading hospital for a particular health care field. Still further, embodiments of the invention can be used to uncover almost any entity, which is desirable for a particular field. For example, embodiments of the present invention can be used to find testifying experts for trials. Geographical areas can also be uncovered for particular expertise. In most embodiments, the invention is easy to use and can be implemented on a computer network, such as a local area network, a wide area network, a world wide area network, any combination of these, and the like. Depending upon the embodiment, one or more of these benefits may be achieved.

Although the above has been described in terms of a healthcare database, many variations can exist. For example, the invention can be implemented using a financial database, an educational database, a legal database, a scientific database, a travel database, a entertainment database, a database of books and the like, a mating database, among others. One of ordinary skill in the art would recognize many other variations, modifications, and alternatives.

While the above is a full description of the specific embodiments, various modifications, alternative constructions and equivalents may be used. Therefore, the above description and illustrations should not be taken as limiting the scope of the present invention which is defined by the appended claims.

What is claimed is:

1. An automated method for identifying and displaying entities having expertise in one or more subjects, the method comprising:
   querying a database for documents relevant to a subject, the documents being indicative of expertise in one or more subject areas;
   calculating a first score for each relevant document based on one or more indicators of expertise in the subject;
   determining entities associated with each relevant document, each of the entities being associated with one or more documents in a set of documents, the entities including at least one institution, at least one author, and at least one geographic region;
   wherein the determining of the at least one institution associated with a relevant document includes determining from a document in the set of documents an affiliated institution of the at least one author;
   wherein determining a geographic region associated with a relevant document includes determining an address of an entity, the address determined at least in part on a document in the set of documents associated with the entity;
   calculating a second score for each entity based on the first scores of the one or more documents in the set of documents associated with each entity;
   calculating a third score for each of a plurality of geographic regions based on the second scores of each entity located within each geographic region;
   ranking expertise associated with the plurality of entities based on the second scores for each entity;
   ranking expertise associated with the plurality of geographic regions based on the third scores for each geographic region;
   hierarchically displaying to a user the ranking of expertise of the plurality of geographic regions;
   wherein the hierarchical displaying includes displaying a user-selectable reference to one or more entities associated with each geographic region, the user-selectable reference to one or more entities further displaying a hierarchical ranking of expertise of the one or more entities associated with the selected geographic region;
   wherein the displaying the ranking of expertise includes at least one of graphically or numerically depicting levels of expertise.

2. The method of claim 1 wherein the database comprises one or more of the following:

the Westlaw database;
the Lexis database; and
the Science Citation Index.

3. The method of claim 1 wherein the database is a Medlars database.

4. The method of claim 1 wherein the database is the Pubmed database.

5. The method of claim 1 wherein the database is a subset of the internet.

6. The method of claim 1 wherein the first score for each relevant document is based on a characteristic of the relevant document.

7. The method of claim 6 wherein the characteristic is a length of the relevant document.

8. The method of claim 6 wherein the characteristic is a publication date or age of the relevant document.

9. The method of claim 6 wherein the characteristic is a type of the relevant document.

10. The method of claim 9 wherein the type is a practice guideline.

11. The method of claim 9 wherein the type is a review.

12. The method of claim 9 wherein the type is a correspondence.

13. The method of claim 1 wherein the first score for each relevant document is based on the characteristic comprises an impact factor of a journal.

14. The method of claim 1 wherein the second score for an author entity is based on a number of authors of a document in the set of documents associated with the author entity.

15. The method of claim 1 wherein the second score for an author entity is based on a rank position of the author entity in the list of authors of a document in the set of documents associated with the author entity.

16. The method of claim 1 wherein the second score for an author entity is based on the author entity being the first author in the list of authors of a document in the set of documents associated with the author entity.

17. The method of claim 1 wherein the second score for an geographical entity is based on a distance from the geographical entity to a geographical location.

18. The method of claim 1 wherein the graphically depicting levels of expertise includes displaying alphanumeric symbols.

19. The method of claim 1 wherein the address is a mailing address.

20. The method of claim 1 wherein the address is an email address.

21. A system for assessing expertise associated with an entity in a subject, the system comprising:
a server system coupled to a database of documents, the server system comprising a memory having stored therein computer-readable code, and a processor for executing the computer-readable code stored in the memory, the computer-readable code comprising:
a first code configured to receive a subject from a user;
a second code configured to query the database for documents relevant to the subject, the documents being indicative of expertise in one or more subject areas;
a third code configured to calculate a first score for each relevant document based on one or more indicators of expertise in the subject;
a fourth code configured to determine entities associated with each relevant document, each of the entities being associated with one or more documents in a set of documents, the entities including at least one institution, at least one author, and at least one geographic region;
wherein the determining of the at least one institution associated with a relevant document includes determining from a document in the set of documents an affiliated institution of the at least one author;
wherein determining a geographic region associated with a relevant document includes determining an address of an entity, the address determined at least in part on a document in the set of documents associated with the entity;
a fifth code configured to calculate a second score for each entity based on the first scores of the one or more documents in the set of documents associated with each entity;
a sixth code configured to calculate a third score for each of a plurality of geographic regions based on the second scores of each entity located within each geographic region;
a seventh code configured to rank expertise associated with the plurality of entities based on the second scores for each entity;
an eighth code configured to rank expertise associated with the plurality of geographic regions based on the third scores for each geographic region; and
a ninth code configured to hierarchically display to a user the ranking of expertise of the plurality of geographic regions;
wherein the hierarchically displaying includes displaying a user-selectable reference to one or more entities associated with each geographic region, the user-selectable reference to one or more entities further displaying a hierarchical ranking of expertise of the one or more entities associated with the selected geographic region;
wherein the displaying the ranking of expertise includes at least one of graphically or numerically depicting levels of expertise.

22. The system of claim 1 wherein the server system is coupled to the database via a world wide network of computers.

23. The system of claim 1 wherein the server system is coupled to a world wide network of computers, and further comprising a user computer coupled with the server system via the worldwide network of computers.

24. The system of claim 23 wherein the first code is configured to receive the subject from the user via the world wide network of computers, and wherein the sixth code is configured to provide to the user the second scores or the ranking of the expertise of the entities via the world wide network of computers.

* * * * *